United States Patent [19]

Hargrave et al.

[11] Patent Number: 5,550,122

[45] Date of Patent: Aug. 27, 1996

[54] PYRIDO[2,3-B][1,5]BENZOXAZEPIN (AND THIAZEPIN)-5(6H)-ONES AND THIONES AND THEIR USE ON THE TREATMENT OF HIV INFECTION

[75] Inventors: Karl D. Hargrave, Brookfield, Conn.; Gunther Schmidt, deceased, late of Munich, Germany, by Margaret Schmidt, legal representative

[73] Assignee: Boehringer Ingelheim Pharmaceuticals, Inc., Ridgefield, Conn.

[21] Appl. No.: 292,123

[22] Filed: Aug. 17, 1994

Related U.S. Application Data

[63] Continuation of Ser. No. 131,263, Oct. 1, 1993, abandoned, which is a continuation of Ser. No. 955,543, Oct. 1, 1992, abandoned, which is a continuation of Ser. No. 562,767, Aug. 6, 1990, abandoned, which is a continuation-in-part of Ser. No. 539,294, Jun. 15, 1990, abandoned, which is a continuation of Ser. No. 400,253, Aug. 29, 1989, abandoned.

[51] Int. Cl.$^6$ .................. A61K 31/55; C07D 513/04; C07D 498/04
[52] U.S. Cl. .................................. 514/211; 540/488
[58] Field of Search .......................... 540/488; 514/211

[56] References Cited

U.S. PATENT DOCUMENTS 5,317,101  5/1994  Oldfield et al. .................. 540/488

Primary Examiner—Robert T. Bond
Attorney, Agent, or Firm—Robert P. Raymond; Mary-Ellen M. Devlin; Alan R. Stempel

[57] ABSTRACT

Disclosed are pyrido[2,3-b][1,5]benzoxazepin (and thiazepin)-5(6H)-ones and -thiones. These are useful in the prevention or treatment of AIDS.

7 Claims, No Drawings

PYRIDO[2,3-B][1,5]BENZOXAZEPIN (AND THIAZEPIN)-5(6H)-ONES AND THIONES AND THEIR USE ON THE TREATMENT OF HIV INFECTION

RELATED APPLICATIONS

This is a continuation of application Ser. No. 131,263, filed Oct. 1, 1993 now abandoned which is a continuation of application Ser. No. 955,543, filed Oct. 1, 1992, now abandoned, which is a continuation of application 562,767, filed Aug. 6, 1990, now abandoned, which is a continuation-in-part of application Ser. No. 539,294, filed Jun. 15, 1990, now abandoned, which is a continuation of application Ser. No. 400,253, filed Aug. 29, 1989, now abandoned.

FIELD OF THE INVENTION

The invention relates to novel pyrido[2,3-b][1,5]benzoxazepin (and thiazepin)-5(6H)-ones and -thiones and pharmaceutically acceptable acid addition salts thereof, methods for preparing these compounds, the use of these compounds in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the vital progeny. These proteins are coded for by the genetic material contained within the infecting virus particle, or virion. Being a retrovirus, however, the genetic material of HIV is RNA, not DNA as in the host cell's genome. Accordingly, the vital RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the vital RNA. Next, acting as a ribonuclease, RT frees the DNA just produced from the original vital RNA and then destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

DESCRIPTION OF THE INVENTION

In its broadest composition of matter aspect, the invention comprises pyrido[2,3b][1,5]benzoxazepin (and thiazepin)-5(6H)-ones and -thiones of the formula I

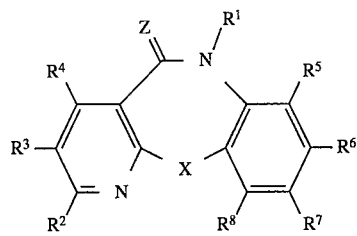

wherein,

X is oxygen or sulfur,

Z is oxygen or sulfur, $R^1$ is alkyl of 1 to 5 carbon atoms, fluoroalkyl of 1 to 3 fluorine atoms and 1 to 5 carbon atoms, cycloalkyl of 3 to 5 carbon atoms, mono- or dihalovinyl, 2-halo-2-propen-1-yl, alkenylmethyl or alkynylmethyl of 3 to 5 carbon atoms, alkyloxyalkyl or alkylthioalkyl of 2 to 4 carbon atoms, arylmethyl (wherein the aryl moiety is phenyl, thienyl or furanyl optionally substituted with methyl, methoxy or halogen), alkoxycarbonylalkyl of 3 to 4 carbon atoms, alkenyloxy- or alkynyloxycarbonyl wherein each alkenyl or alkynyl moiety contains 2 to 4 carbon atoms, hydroxy, alkoxy of 1 to 4 carbon atoms, amino, mono- or di-alkylamino wherein each alkyl moiety contains 1 to 3 carbon atoms, aminocarbonylmethyl, alkanoylaminoalkyl wherein the alkanoyl moiety contains 2 to 3 carbon atoms and the alkyl moiety contains 1 to 2 carbon atoms, hydroxyalkylmethyl of 2 to 5 carbon atoms, alkanoyl of 2 to 3 carbon atoms, or cyanoalkyl wherein the alkyl moiety contains 1 to 4 carbon atoms;

one of $R^2$, $R^3$ and $R^4$ is alkyl of 1 to 4 carbon atoms, alkenyl or alkynyl of 2 to 4 carbon atoms, halogen, hydroxyl, alkoxy or alkylthio of 1 to 3 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono-or dimethylaminomethyl, hydroxyalkyl of 1 to 4 carbon atoms, alkoxyalkyl or alkylthioalkyl wherein each alkyl moiety contains 1 to 2 carbon atoms, alkoxycarbonyl of 2 to 3 carbon atoms, trihalomethyl, alkanoyl of 2 to 3 carbon atoms, alkanoylamino of 1 to 3 carbon atoms, cyano, azido, alkoxycarbonylmethyl of 3 to 4 carbon atoms or methoxycarbonylmethoxy, with one of the two remaining groups being hydrogen or methyl and the last remaining group being hydrogen; or, two of $R^2$, $R^3$ and $R^4$ are methyl, ethyl or chloro, with the remaining group being hydrogen; or, $R^2$, $R^3$ and $R^4$ are each hydrogen; and, one of $R^5$, $R^6$, $R^7$ and $R^8$ is alkyl of 1 to 4 carbon atoms, alkenyl or alkynyl of 2 to 4 atoms, halogen, hydroxyl, alkoxy or alkylthio of 1 to 3 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono-or dimethylaminomethyl, hydroxyalkyl of 1 to 4 carbon atoms, alkoxyalkyl or alkylthioalkyl wherein each alkyl moiety contains 1 to 2 carbon atoms, alkoxycarbonyl of 2 to 3 carbon atoms, trihalomethyl, alkanoyl of 2 to 3 carbon atoms, alkanoylamino of 1 to 3 carbon atoms, cyano, azido, alkoxycarbonylmethyl of 3 to 4 carbon atoms or methoxycarbonylmethoxy, with one of the three remaining groups being hydrogen, methyl, ethyl or chloro and the other two remaining groups being hydrogen; or, $R^5$, $R^6$, $R^7$ and $R^8$ are each hydrogen.

A subgeneric aspect of the invention comprises compounds of formula I, wherein

X is oxygen or sulfur,

Z is oxygen or sulfur;

$R^1$ is alkyl of 1 to 4 carbon atoms, fluoroalkylmethyl of 1 to 3 fluorine atoms and 2 to 4 carbon atoms, mono- or dihalovinyl, 2-halo-2-propen-1-yl, alkenylmethyl or alkynylmethyl of 3 to 4 carbon atoms, alkyloxyalkyl or alkylthioalkyl of 2 to 4 carbon atoms, alkoxycarbonylalkyl of 3 to 4 carbon atoms, alkenyloxy- or alkynyloxycarbonyl wherein each alkenyl or alkynyl moiety contains 2 to 4 carbon atoms, aminocarbonylmethyl, alkanoylaminoalkyl wherein the alkanoyl moiety contains 2 to 3 carbon atoms and the alkyl moiety contains 1 to 2 carbon atoms, hydroxyalkylmethyl of 2 to 4 carbon atoms, alkanoyl of 2 to 3 carbon atoms, or cyanoalkyl wherein the alkyl moiety contains 1 to 4 carbon atoms;

one of $R^2$, $R^3$ and $R^4$ is alkyl of 1 to 3 carbon atoms, alkenyl or alkynyl of 2 to 3 carbon atoms, halogen, hydroxyl, alkoxy or alkylthio of 1 to 2 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono- or dimethylaminomethyl, hydroxyalkyl of 1 to 3 carbon atoms, alkoxyalkyl or alkylthioalkyl of 2 to 3 carbon atoms, trihalomethyl, acetyl, alkanoylamino of 1 to 3 carbon atoms, cyano, azido or methoxycarbonylmethoxy, with one of the two remaining groups being hydrogen or methyl and the last remaining group being hydrogen; or, two of $R^2$, $R^3$ and $R^4$ are methyl, ethyl or chloro, with the remaining group being hydrogen; or, and $R^2$, $R^3$ and $R^4$ are each hydrogen; and, one of $R^5$, $R^6$, $R^7$ and $R^8$ is alkyl of 1 to 3 carbon atoms, alkenyl or alkynyl of 2 to 3 atoms, halogen, hydroxyl, alkoxy or alkylthio of 1 to 2 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono-or dimethylaminomethyl, hydroxyalkyl of 1 to 3 carbon atoms, alkoxyalkyl or alkylthioalkyl of 2 to 3 carbon atoms, trihalomethyl, acetyl, alkanoylamino of 1 to 3 carbon atoms, cyano, azido or methoxycarbonylmethoxy, with one of the three remaining groups being hydrogen, methyl, ethyl or chloro and the other two remaining groups being hydrogen; or, $R^5$, $R^6$, $R^7$ and $R^8$ are each hydrogen.

A further subgeneric aspect of the invention comprises compounds of formula I, wherein X is oxygen or sulfur, Z is oxygen;

$R^1$ is alkyl of 1 to 4 carbon atoms, fluoroalkylmethyl of 1 to 3 fluorine atoms and 2 to 4 carbon atoms, mono- or dihalovinyl, 2-halo-2-propen-1-yl, alkenylmethyl or alkynylmethyl of 3 to 4 carbon atoms, alkyloxyalkyl or alkylthioalkyl of 2 to 4 carbon atoms, aminocarbonylmethyl, or cyanoalkyl wherein the alkyl moiety contains 1 to 3 carbon atoms;

one of $R^2$, $R^3$ and $R^4$ is methyl, ethyl, chloro, or amino, with the two remaining groups being hydrogen; or, two of $R^2$, $R^3$ and $R^4$ are methyl, ethyl or chloro, with the remaining group being hydrogen; or, $R^2$, $R^3$ and $R^4$ are each hydrogen; and, one of $R^5$, $R^6$, $R^7$ and $R^8$ is methyl, ethyl, chloro, or amino, with the three remaining groups being hydrogen; or, two of $R^5$, $R^6$, $R^7$ and $R^8$ are methyl, ethyl or chloro, with the remaining two groups being hydrogen; or, $R^5$, $R^6$, $R^7$ and $R^8$ are each hydrogen.

A still further subgeneric aspect of the invention comprises compounds of formula I, wherein X is oxygen or sulfur;, Z is oxygen;

$R^1$ is alkyl of 1 to 4 carbon atoms, allyl, or alkylthioalkyl of 2 to 4 carbon atoms;

$R^2$ and $R^4$ are hydrogen;

$R^3$ is hydrogen or amino;

$R^5$ and $R^7$ are hydrogen or methyl; and, $R^6$ and $R^8$ are hydrogen.

The compounds of formula I can be prepared by known methods or obvious modifications thereof. Methods A,B, C,D and E, described below, are illustrative of methods for preparing compounds of formula I.

Method A

Compounds of formula I, wherein Z is oxygen and X and $R^1$–$R^8$ have the meanings given above, may be obtained, for example, by converting a compound of the formula II

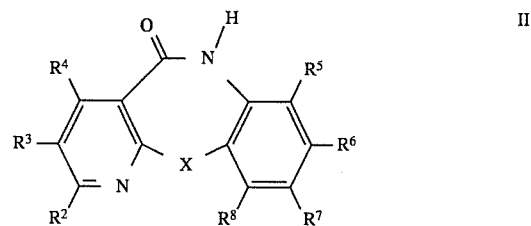

wherein $R^2$–$R^8$ are as defined above, into the corresponding alkali or alkaline earth metal compounds of the formula III

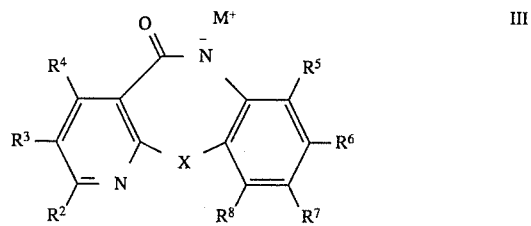

wherein $R^2$–$R^8$ are as defined above, and subsequently reacting, without isolation, this alkali metal compound with a reactive alkylating or acylating reagent of the formula IV

$R^1Y$      IV wherein $R^1$ has the meanings defined above, and Y is a suitable leaving group such as chloride, bromide, iodide, an alkyl or arylsulfonate, or an alkylcarbonyloxy or arylcarbonyloxy group, under well known alkylating or acylating conditions.

It will be obvious to those skilled in the art that the presence of nucleophilic substituents in the compounds of formulas II, for example, will require the use of an intermediate having substituents which are, other than the 5-position nitrogen, not nucleophilic but which can be derivatized to yield the required group. For example, amino or monoalkylamino substituents are preferably obtained by alkylating or acylating an intermediate of formula II having nitro group(s) at the desired positions, and subsequently reducing the nitro group(s), and alkylating, if appropriate, to yield the final product.

Method B

Compounds of formula I wherein Z is oxygen and X and $R^1$–$R^6$ are as defined above may be obtained by cyclization of compounds of the formula V

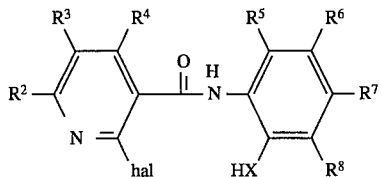

wherein X and $R^1$–$R^8$ are as defined above and hal is fluorine, chlorine, bromine or iodine, preferably in the presence of an inorganic base, such as sodium or potassium hydride, lithium alkyls such as n-butyl lithium sodium or potassium hydroxide, or in the presence of an organic base, such as quinoline or 4-(N-N-dimethylamino) pyridine, at ambient or elevated temperatures, preferably 80°–175° C., up to the boiling point of the boiling point of the reaction mixture. Suitable solvents include inert aprotic solvents such as toluene, sulfolane or dimethylformamide.

The pyridophenylamides of formula V may be obtained, for example, by condensing suitably substituted 2-halonicotinic acid chlorides of the formula VI

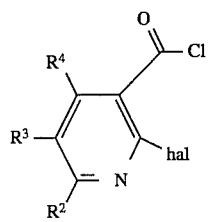

wherein hal may be fluorine, chlorine, bromine or iodine and $R^2$–$R^4$ are as defined above, with ortho-aminophenols (or thiophenols) of the formula VII

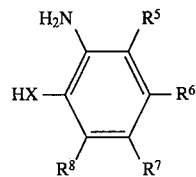

wherein X, $R^1$ and $R^5$–$R^8$ are as defined above under well-known reaction conditions. Depending upon the reaction conditions utilized and the nature of X and $R^1$–$R^8$, tricyclic compounds of the formula I, wherein X, $R^1$–$R^8$ are as defined above, may be formed in one step, without the isolation of the amide of formula V, by the condensation of compounds of the formulas VI and VII. This single-step formation of the tricyclic compound is most readily effected when X is sulfur and at elevated temperatures, especially in the range of 80°–175° C.

Method C

Thiolactams of formula I, wherein Z is sulfur and X and $R^1$–$R^8$ are as defined above, can be obtained treatment of lactams of the formula I with sulfurating reagents such as 2,4-bis(4-methoxyphenyl)-1, 3-dithia-2,4-diphosphetane-2,4-disulfide, bis(tricyclohexyltin)sulfide, bis( tri-n-butyltin)sulfide, bis(triphenyltin)sulfide bis(trimethylsilyl)sulfide and phosphorous pentasulfide. The reaction is generally carried out under anhydrous conditions in inert organic solvents such as carbon disulfide, benzene, or toluene, for example at room temperature or, preferably, higher temperatures up to the boiling point of the reaction mixture. When using the above mentioned tin or silyl sulfides it is preferable to carry out the sulfurization reaction in the presence of a Lewis acid such as boron trichloride.

It will be obvious to those skilled in the art that the presence of another carbonyl moiety in a compound of formula I, for example, a compound wherein Z is oxygen and any of $R^1$–$R^8$ contains a carbonyl moiety, will require that the ketone carbonyl be protected via known methods prior to the sulfurization reaction; deprotection subsequent to the sulfurization reaction provides the desired compound. Similarly, in cases wherein $R^1$ is, for example, acetyl, it will be obvious that the sulfurization reaction should be performed prior to the acylation (of N-5). In those cases wherein the substituents at $R^2$ to $R^8$ can be derived from nitro, for example, alkanoylamino, the sulfurization reaction can be performed on the corresponding nitro derivative, followed by an appropriate (known) reduction and finally acylation to yield the desired product.

Compounds of formula I may, if desired, be converted into their pharmaceutically acceptable salts by conventional methods. The invention comprises such salts.

Examples of inorganic and organic acids which may form nontoxic, pharmaceutically acceptable acid addition salts with a compound of the formula I are the following: hydrochloric acid, hydrobromic acid, sulfuric acid, phosphoric acid, nitric acid, tartaric acid, citric acid, methanesulfonic acid, and the like.

Examples of bases which may form pharmaceutically acceptable salts with compounds of formula I having acidic substituents are the following: sodium hydroxide, potassium hydroxide, calcium hydroxide, ammonia, tromethamine and the like.

The above described compounds of formula I possess inhibitory activity against HIV-1 reverse transciptase. When administered in suitable dosage forms, they are useful in the prevention or treatment of AIDS, ARC and related disorders associated with HIV-1 infection. Another aspect of the invention, therefore, is a method for preventing or treating HIV-1 infection which comprises administering to a human being, exposed to or infected by HIV-1, a prophylactically or therapeutically effective amount of a novel compound of Formula I, as described above.

The compounds of formula I may be administered in single or divided doses by the oral, parenteral or topical routes. A suitable oral dosage for a compound of formula I would be in the range of about 0.5 mg to 1 g per day. In parenteral formulations, a suitable dosage unit may contain from 0.1 to 250 mg of said compounds, whereas for topical administration, formulations containing 0.01 to 1% active ingredient am preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid career material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is believed that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAY

Assay Theory:

Among the enzymes for which Human Immunodeficiency Virus (HIV-1 ) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials:

a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprt1+ (2) which is under the control of the lac promotor in the expression vector pIBI21 (4). An overnight culture grown in 2XYT medium (37° C., 225 rpm) (5) supplemented with 100 µg/ml ampicillin for positive selection is inoculated at a 1:40 dilution into M9 medium supplemented with 10 µg/ml thiamine, 0.5% casamino acids, and 50 µg/ml ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375 M NaCl buffer and digested by the addition of lysozyme (1 mg/ml) for 30 minutes on ice. The cells are lysed by the addition of 0.2% NP-40 and brought to 1 M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2×concentrated stock reaction mixture

| Stock Reagent | 2X Mix Concentration |
|---|---|
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 µg/ml |
| $^3$H-dGTP (81 µM) | 0.6 µM |

Assay Procedure:

The 2×concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10µl/well; 3 wells/compound). The HIV-1 RT enzyme is thawed, diluted in 50mM Tris pH 7.4 so that fifteen µl of diluted enzyme contain 0.001 Unit (one unit is that amount of enzyme to transform 1 micromole of substrate per minute at 25° C.), and fifteen µl are dispensed per well. Twenty µl of 0.12–0.5 M EDTA are added to the first three wells of the microliter plate. EDTA chelates the Mg$^{++}$present and prevents reverse transcription. This group serves as background polymerization which is subtracted from all other groups. Twenty-five ul of the 2×reaction mixture are added to all wells and the assay is allowed to incubate at room temperature for 60 minutes. The assay is terminated by precipitating the DNA in each well with 50 µl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value} \times 100}{CPM \text{ Mean Control Value}}$$

References:

1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T, Fritsch, E. F., and J. Sambrook, eds. *Molecular Cloning: A Laboratory Manual*, Cold Spring Harbor Laboratory, 1982.
6. Spira, T., et at. J. *Clinical Microbiology*, 25:97, 1987.

In order to roughly assess the cytotoxicity of the compounds provided by the invention, several such compounds were tested in the MTT Cellular Cytotoxicity Assay described below. The results of this testing are reported in Table I, below. Compounds having a relatively high $EC_{50}$ are preferred.

MTT ASSAY FOR CELLULAR CYTOTOXICITY

Assay Theory:

The MTT [3-(4,5-dimethylthiazol-2-yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method:

The H9 cell line (2), an established human lymphoma suspension cell line grown in RPMI 1640 supplemented with 10% fetal bovine serum, is used as the target cell line in the assay. Cells (100μl) are plated in microtest plate wells at a concentration of $10^5$ cells per ml in the presence of varying concentrations of inhibitor. The cells are incubated at 37° C. in a humidified $CO_2$ incubator. Five days later, 20μl of MTT (5mg/ml in RPMI 1640, sonicated, 0.2 micron filtered, and stored at 4° C.) is added to each well. After 4 hours additional incubation at 37° C., 60μl of Triton-X is added to each well and thoroughly mixed to aid the solubilization of the crystals. Absolute ethanol (5μl) is added to each well and the resulting mixture is incubated for 30 minutes at 60° C. and immediately read on a plate reader (Dynatech) at a wavelength of 570 nm. Data from this assay are used to generate a nonlinear regression analysis which yields an $EC_{50}$.

References:

1. Mosmann, Tim, *J. Immunol.* Methods, 65:55, 1983.
2. Jacobs, J. P., *J. Natl. Cancer Inst.*, 34:231, 1965.

TABLE I

| Compound of Example No. | RT Inhibition % @ 10 μg/ml | Cytotoxicity Assay ($EC_{50}$) |
|---|---|---|
| 1 | 80 | NT |
| 2 | 89 | NT |
| 3 | 57* | 315 μM |
| 4 | 92* | NT |
| 5 | 93* | NT |
| 6 | 82* | NT |
| 7 | 71 | NT |
| 8 | 77 | NT |
| 9 | 89 | NT |
| 10 | 28 | NT |
| 11 | 43* | NT |
| 12 | 67* | NT |
| 13 | 41† | NT |
| 14 | 33* | NT |
| 15 | 85 | NT |

Note: NT = not tested
*% inh. @ 1 μM
†% inh. @ 2.5 μM

The following examples further illustrate the present invention and will enable others skilled in the art to understand it more completely. It should be understood, however, that the invention is not limited to the particular examples given below.

EXAMPLE 1

6-(n-Propyl)pyrido[2,3-b][1,5]benzoxazepin- 5(6H)-one

Sodium hydride (0.96 g of a 50% suspension in mineral oil) was added to a solution of 2.12 g of pyrido[2,3-b][1,5]benzoxazepin-5(6H)-one (synthesized according to published procedures) in 50 ml of dimethylformamide and the resulting mixture stirred for 1 h. 1-Bromopropanol (2.46 g) was slowly added and the reaction mixture allowed to stir overnight at room temperature. Crashed ice was added to decompose unreacted sodium hydride. Water was then added and the product was extracted with ether, dried (anhydrous sodium sulfate) and concentrated in vacuo. Purification on a silica gel column (ethyl acetate/hexane, 1:4) provided 1.52 g as a viscous, colorless oil.

EXAMPLE 2

6-Ethylpyrido[2,3-b ][1,5]benzothiazepin -5( 6H)-one a) Pyrido[2,3-b][1,5]benzothiazepin-5(6H)-one A mixture of 2-chloronicotinic acid (31.5 g, 0.2 mol) and thionyl chloride (100 ml) was refluxed for 3 hours. The solvent was removed in vacuo and the acid chloride was then added to a mixture of 2-aminothiophenol (25 g), toluene (400 ml) and pyridine (34 g). The resulting mixture was refluxed for 4 hours and allowed to stand overnight at room temperature. The yellow precipitate was collected and stirred with water for 3 hours, filtered and air dried. The product was recrystallized from ethyl acetate to give 20.8 g (45% of theory) of almost pure yellow product, suitable for use in the next reaction. A small amount of this product was recrystallized from acetonitrile to give pure product as light yellow solid, m.p. 260°–261° C.

b) 6-Ethylpyrido[2,3-b][1,5]benzothiazepin-5(6H)-one

Sodium hydride (1.05 g of a 50% suspension in mineral oil) was added to a suspension of pyrido[2,3-b][1,5]benzothiazepin-5(6H)-one (4.0 g, 0.0175 mol) in 100 ml of dimethylformamide and the resulting mixture stirred until the evolution of gas stopped, at which time the mixture was heated to 50° C. for 30 min. After cooling to room temperature, ethyl iodide (5.46 g, 0.035 mol) was slowly added and the reaction mixture allowed to stir for 2 hours. Crushed ice was added to decompose unreacted sodium hydride. Water was then added and the product was extracted with ether, dried (anhydrous sodium sulfate) and concentrated in vacuo. After washing the solid residue with hexane, it was recrystallized from ethyl acetate/hexane to give 0.66 g (14% of theory) of product as yellow crystals, m.p. 148°–149° C.

EXAMPLE 3

3-Amino-6,9-dimethylpyrido[2,3-b][1,5]benzoxazepin-5(6H)-one a) 2-Hydroxy-5-nitronicotinic acid Fuming nitric acid (d 1.5, 10 ml, 0.24 mol) was added to a solution of 2-hydroxynicotinic acid (14 g, 0.1 mol) and conc. sulfuric acid (40 ml). The resulting mixture was heated at 50° C for 4 hours, and then carefully poured into ice water. The light orange precipitate was collected, washed with cold water and then recrystallized from water to give 13.3 g (72% of theory) of nearly pure product as pale yellow crystals, m.p. 240° C., suitable for use in the next reaction.

b) 2-Chloro-5-nitronicotinic acid

A solution of 2-hydroxy-5-nitronicotinic acid (9.2 g, 0.05 mol) in phosphorus oxychloride (25 ml) was refluxed for 5 hours. The solvent was removed in vacuo and the residue dissolved in a mixture of tetrahydrofuran and ether. After cooling the solution in an ice bath, water was cautiously added dropwise with stirring until a clean separation of layers was obtained. The organic layer was washed with water and a saturated sodium chloride solution, dried (anhydrous magnesium sulfate) and concentrated. Recrystallization from ether gave 6.94 g (69% of theory) of pure product, m.p. 135° C. (dec).

c) 2-Chloro-5-nitro-N-(3-hydroxytol-4-yl)-3-pyridinecarboxamide

A mixture of 2-chloro-5-nitronicotinic acid (6.1 g, 0.03 mol) and thionyl chloride (15 ml) was refluxed for 3 hours. The solvent was removed in vacuo and the acid chloride was dissolved in tetrahydrofuran (150 ml). The resulting solution was slowly added to a solution of 6-amino-m-cresol (4 g, 0.03 mol), N,N-diisopropylethylamine (7 ml, 0.04 mol), and tetrahydrofuran (150 ml) at 0° C. under argon, and the resulting solution stirred for 2 hours. The mixture was then diluted with water and the product was extracted with ether, washed with a saturated sodium chloride solution, dried (anhydrous magnesium sulfate), and concentrated to half volume. The gummy orange crude product was collected and stirred with methylene chloride (50 ml) for 30 min. The precipitate was washed with methylene chloride and air dried to give 6.3 g (68% of theory) of pure product as a bright orange powder.

d) 3-Nitro-9-methylpyrido[2,3-b][1,5]benzoxazepin-5(6H)-one

A mixture of 2-chloro-5-nitro-N-(3-hydroxytol-4-yl)-3-pyridinecarboxamide (6.3 g, 0.02 mol) and pyridine (100 ml) was heated under argon at 90° C. for 2.5 hours. The cooled solution was diluted with water and the yellow-orange precipitate collected and washed with water. The solid was then stirred in hot water (100 ml) for 45 min., filtered and washed with ethanol and ether to give 4.3 g of a tan-brown solid. Recrystallization from dimethylformamide/water afforded 3.76 g (69% of theory) of product.

e) 3-Nitro-6,9-dimethylpyrido[2,3-b][1,5]benzoxazepin-5(6H)-one

To a suspension of sodium hydride (0.73 g, 0.015 mol of a 50% dispersion in mineral oil) in dimethylformamide (75 ml) under argon was added in one portion 3-Nitro-9-methylpyrido[2,3-b][1,5]benzoxazepin-5(6H)-one (3.75 g, 0.014 mol). Methyl iodide (1.3 ml. 0.021 mol) was added, and the resulting solution was stirred overnight at room temperature. The mixture was diluted with ice Water, and the precipitated product was collected and washed with water and pet ether. The crude product was recrystallized from ethyl acetate to give 3.14 g (79% of theory) of the product as a pale yellow solid. m.p. 197°–198° C.

f) 3-Amino-6,9-dimethylpyrido[2,3-b][1,5]benzoxazepin-5(6H)-one

To a suspension of 3-nitro-6,9-dimethylpyrido[2,3-b][1,5]benzoxazepin-5(6H)-one (1.6 g, 5.6 mmol) in acetic acid (30 ml) was added a solution of stannous chloride dihydrate (10 g, 44 mmol) in conc. hydrochloric acid (13 ml). After stirring the mixture for 3 hours, the precipitated product was filtered and washed with ether. The product was then dissolved in water, basified with 2N sodium hydroxide, extracted with ether and ethyl acetate, dried (anhydrous magnesium sulfate), and concentrated. Crystallization from ethanol/hexane provided 0.82 g (57% of theory) of pure product as tan needles, m.p. 191°–193° C.

EXAMPLES 4–15

The compounds of the following examples were prepared by procedures analogous to those described above:

EXAMPLE NO.

4. 3-Amino-6,7,9-trimethylpyrido[2,3-b][1,5]benzoxazepin-5(6H)-one, m.p. 234–236° C.
5. 3-Amino-7,9-dimethyl-6-Ethylpyrido[2,3-b][1,5]benzoxazepin-5(6H)-one, m.p. 232°–234° C.
6. 3-Amino-7,9-dimethyl-6-(n-propyl)pyrido[2,3-b ][1,5]benzoxazepin-5(6H)-one, m.p. 195°–197° C.
7. 6-Methylpyrido[2,3-b][1,5]benzoxazepin-5(6H)-one, m.p. 107°–109° C.
8. 6-Ethylpyrido[2.3-b][1,5]benzoxazepin-5(6H)-one, m.p. 81°–81° C.
9. 6-Allylpyrido[2,3-b][1,5]benzoxazepin-5(6H)-one, m.p. 58°–60° C.
10. 6-Propionylpyrido[2,3-b][1,5]benzoxazepin-5(6H)-one, m.p. 111°–113° C.
11. 6,9-Dimethylpyrido[2,3-b][1,5]benzoxazepin-5(6H)-one, m.p. 165°–168° C.
12. 6-Ethyl-9-methylpyrido[2,3-b][1,5]benzoxazepin-5(6H)-one, m.p. 114°–116° C.
13. 3-Hydroxy-6,9-dimethylpyrido[2,3-b][1,5]benzoxazepin-5(6H)-one, m.p. 257–258.5° C.
14. 7-Amino-6-ethylpyrido[2,3-b][1,5]benzoxazepin-5(6H)-one, m.p. 114°–116° C.
15. 6-Methylpyrido[2,3-b][1,5]benzothiazepin-5(6H)-one, m.p. 172°–174° C.

EXAMPLE 16

3-Amino-6,9-dimethylpyrido[2,3,-b][1,5]benzothiazepin-5(6H)-one

Using a procedure analogous to that of Example 3, but employing 2-mercapto-5-nitronicotinic acid as starting material, the title compound could be made.

EXAMPLE 17-21

Using procedures analogous to those described above, the following compounds could be made.

EXAMPLE NO.

17. 3-Amino-6,7,9-trimethylpyrido[2,3-b][1,5]benzothiazepin-5(6H)-one
18. 3-Amino-7,9-dimethyl-6-ethylpyrido[2,3-b][1,5]benzoxazepin-5(6H)-one
19. 3-Amino-7,9-dimethyl-6-(n-propyl)pyrido[2,3-b][1,5] benzothiazepin-5(6H)-one
20. 3-Amino-7,9-dimethyl-6-(i-propyl)pyrido[2,3-b ][1,5] benzothiazepin-5(6H)-one
21. 3-Amino-7,9-dimethyl-6-allylpyrido[2,3-b ][1,5]benzothiazepin-5(6H)-one

EXAMPLE A

| Capsules or Tablets | | | |
|---|---|---|---|
| A-1 Ingredients | Quantity | A-2 Ingredients | Quantity |
| Compound of Example 1 | 50 mg | Example 1 | 50 mg |
| Starch | 160 mg | Dicalcium Phosphate | 160 mg |
| Microcrys, Cellulose | 90 mg | Microcrys. Cellulose | 90 mg |
| Sodium Starch Gluctate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 1 is blended into a powder mixture with the premixed excipient materials as identified above with the exception of the lubricant. The lubricant is then blended in and the resulting blend compressed into tablets or filed into hard gelatin capsules.

EXAMPLE B

| Parenteral Solutions | |
|---|---|
| Ingredients | Quantity |
| Compound of Example 1 | 500 mg |
| Tartaric acid | 1.5 g |
| Benzyl Alcohol | 0.1% by weight |
| Water for injection | q.s. to 100 ml |

The excipient materials are mixed with the water and thereafter the compound of Example 1 is added. Mixing is continued until the solution is clear. The pH of this solution is adjusted to 3.0 and is then filtered into the appropriate vials or ampoules and sterilized by autoclaving.

EXAMPLE C

| Nasal Solutions | |
|---|---|
| Ingredients | Quantity |
| Compound of Example 1 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 ml |

The excipient materials are mixed with the water and thereafter the compound of Example 1 is added and mixing is continued until the solution is clear. The pH of this solution is adjusted to 4.0 and is then filtered into the appropriate vials or ampoules.

We claim:

1. A compound of the formula I

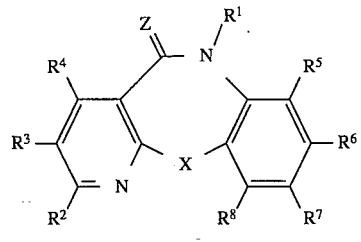

wherein,

X is oxygen or sulfur;

Z is oxygen or sulfur;

$R^1$ is alkyl of 1 to 5 carbon atoms, fluoroalkyl of 1 to 3 fluorine atoms and 1 to 5 carbon atoms, cycloalkyl of 3 to 5 carbon atoms, mono- or dihalovinyl, 2-halo-2-propen-1-yl, alkenylmethyl or alkynylmethyl of 3 to 5 carbon atoms, alkyloxyalkyl or alkylthioalkyl of 2 to 4 carbon atoms, arylmethyl (wherein the aryl moiety is phenyl, thienyl or furanyl optionally substituted with methyl, methoxy or halogen), alkoxycarbonylalkyl of 3 to 4 carbon atoms, alkenyloxy- or alkynyloxycarbonyl wherein each alkenyl or alkynyl moiety contains 2 to 4 carbon atoms, hydroxy, alkoxy of 1 to 4 carbon atoms, amino, mono- or di-alkylamino wherein each alkyl moiety contains 1 to 3 carbon atoms, aminocarbonylmethyl, alkanoylaminoalkyl wherein the alkanoyl moiety contains 2 to 3 carbon atoms and the alkyl moiety contains 1 to 2 carbon atoms, hydroxyalkylmethyl of 2 to 5 carbon atoms, alkanoyl of 2 to 3 carbon atoms, or cyanoalkyl wherein the alkyl moiety contains 1 to 4 carbon atoms;

one of $R^2$, $R^3$ and $R^4$ is alkyl of 1 to 4 carbon atoms, alkenyl or alkynyl of 2 to 4 carbon atoms, halogen, hydroxyl, alkoxy or alkylthio of 1 to 3 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono- or dimethylaminomethyl, hydroxyalkyl of 1 to 4 carbon atoms, alkoxyalkyl or alkylthioalkyl wherein each alkyl moiety contains 1 to 2 carbon atoms, alkoxycarbonyl of 2 to 3 carbon atoms, trihalomethyl, alkanoyl of 2 to 3 carbon atoms, alkanoylamino of 1 to 3 carbon atoms, cyano, azido, alkoxycarbonylmethyl of 3 to 4 carbon atoms or methoxycarbonylmethoxy, with one of the two remaining groups being hydrogen or methyl and the last remaining group being hydrogen; or, two of $R^2$, $R^3$ and $R^4$ are methyl, ethyl or chloro, with the remaining group being hydrogen; or, $R^2$, $R^3$ and $R^4$ are each hydrogen; and, one of $R^5$, $R^6$, $R^7$ and $R^8$ is alkyl of 1 to 4 carbon atoms, alkenyl or alkynyl of 2 to 4 carbon atoms, halogen, hydroxyl, alkoxy or alkylthio of 1 to 3 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono- or dimethylaminomethyl, hydroxyalkyl of 1 to 4 carbon atoms, alkoxyalkyl or alkylthioalkyl wherein each alkyl moiety contains 1 to 2 carbon atoms, alkoxycarbonyl of 2 to 3 carbon atoms, trihalomethyl, alkanoyl of 2 to 3 carbon atoms, alkanoylamino of 1 to 3 carbon atoms, cyano, azido, alkoxycarbonylmethyl of 3 to 4 carbon atoms or methoxycarbonylmethoxy, with one of the three remaining groups being hydrogen, methyl, ethyl or chloro and the other two remaining groups being hydrogen; or, $R^5$, $R^6$, $R^7$ and $R^8$ are each hydrogen;

or a pharmaceutically acceptable salt thereof.

2. A compound of formula, in accordance with claim 1, wherein,

X is oxygen or sulfur;

Z is oxygen or sulfur;

$R^1$ is alkyl of 1 to 4 carbon atoms, fluoroalkylmethyl of 1 to 3 fluorine atoms and 2 to 4 carbon atoms, mono- or dihalovinyl, 2-halo-2-propen-1-yl, alkenylmethyl or alkynylmethyl of 3 to 4 carbon atoms, alkyloxyalkyl or alkylthioalkyl of 2 to 4 carbon atoms, alkoxycarbonylalkyl of 3 to 4 carbon atoms, alkenyloxy- or alkynyloxycarbonyl wherein each alkenyl or alkynyl moiety contains 2 to 4 carbon atoms, aminocarbonylmethyl, alkanoylaminoalkyl wherein the alkanoyl moiety contains 2 to 3 carbon atoms and the alkyl moiety contains 1 to 2 carbon atoms, hydroxyalkylmethyl of 2 to 4 carbon atoms, alkanoyl of 2 to 3 carbon atoms, or cyanoalkyl wherein the alkyl moiety contains 1 to 4 carbon atoms;

one of $R^2$, $R^3$ and $R^4$ is alkyl of 1 to 3 carbon atoms, alkenyl or alkynyl of 2 to 3 carbon atoms, halogen, hydroxyl, alkoxy or alkylthio of 1 to 2 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono- or dimethylaminomethyl, hydroxyalkyl of 1 to 3 carbon atoms, alkoxyalkyl or alkylthioalkyl of 2 to 3 carbon atoms, trihalomethyl, acetyl, alkanoylamino of 1 to 3 carbon atoms, cyano, azido or methoxycarbonylmethoxy, with one of the two remaining groups being hydrogen or methyl and the last remaining group being hydrogen; or, two of $R^2$, $R^3$ and $R^4$ are methyl, ethyl or chloro, with the remaining group being hydrogen; or, $R^2$, $R^3$ and $R^4$ are each hydrogen; and, one of $R^5$, $R^6$, $R^7$ and $R^8$ is alkyl of 1 to 3 carbon atoms, alkenyl or alkynyl of 2 to 3 carbon atoms, halogen, hydroxyl, alkoxy or alkylthio of 1 to 2 carbon atoms, alkanoyloxy of 2 to 3 carbon atoms, amino, mono- or di-alkylamino wherein each alkyl moiety contains 1 to 2 carbon atoms, aminoalkyl of 1 to 2 carbon atoms, mono- or dimethylaminomethyl, hydroxyalkyl of 1 to 3 carbon atoms, alkoxyalkyl or alkylthioalkyl of 2 to 3 carbon atoms, trihalomethyl, acetyl, alkanoylamino of 1 to 3 carbon atoms, cyano, azido or methoxycarbonylmethoxy, with one of the three remaining groups being hydrogen, methyl, ethyl or chloro and the other two remaining groups being hydrogen; or, $R^5$, $R^6$, $R^7$ and $R^8$ are each hydrogen.

3. A compound of formula I, in accordance with claim 1, wherein

X is oxygen or sulfur;

Z is oxygen;

$R^1$ is alkyl of 1 to 4 carbon atoms, fluoroalkylmethyl of 1 to 3 fluorine atoms and 2 to 4 carbon atoms, mono- or dihalovinyl, 2-halo-2-propen-1-yl, alkenylmethyl or alkynylmethyl of 3 to 4 carbon atoms, alkyloxyalkyl or alkylthioalkyl of 2 to 4 carbon atoms, aminocarbonylmethyl, or cyanoalkyl wherein the alkyl moiety contains 1 to 3 carbon atoms;

one of $R^2$, $R^3$ and $R^4$ is methyl, ethyl, chloro, or amino, with the two remaining groups being hydrogen; or, two of $R^2$, $R^3$ and $R^4$ are methyl ethyl or chloro, with the remaining group being hydrogen; or, $R^2$, $R^3$ and $R^4$ are each hydrogen; and, one of $R^5$, $R^6$, $R^7$ and $R^8$ is methyl, ethyl, chloro, or amino, with the three remaining groups being hydrogen; or, two of $R^5$, $R^6$, $R^7$ and $R^8$ are methyl, ethyl or chloro, with the remaining two groups being hydrogen; or, $R^5$, $R^6$, $R^7$ and $R^8$ are each hydrogen.

4. A compound of formula I, in accordance with claim 1, wherein

X is oxygen or sulfur;

Z is oxygen;

$R^1$ is alkyl of 1 to 4 carbon atoms, allyl, or alkylthioalkyl of 2 to 4 carbon atoms;

$R^2$ and $R^4$ are hydrogen;

$R^3$ is hydrogen or amino;

$R^5$ and $R^7$ are hydrogen or methyl; and, $R^6$ and $R^8$ are hydrogen.

5. A compound selected from the group consisting of the following:

3-Amino-6,9-dimethylpyrido[2,3-b][1,5]benzoxazepin-5(6H)-one;

3-Amino-6,7,9-trimethylpyrido[2,3-b][1,5]benzoxazepin-5(6H)-one;

3-Amino-7,9-dimethyl-6-ethylpyrido[2,3-b][1,5]benzoxazepin-5(6H)one;

3-Ammo-7,9-dimethyl-6-(n-propyl)pyrido[2,3-b][1,5]benzoxazepin-5(6H)-one;

3-Amino-6,9-dimethylpyrido[2,3-b][1,5]benzothiazepin-5(6H)-one;

3-Amino-6,7,9-trimethylpyrido[2,3-b][1,5]benzothiazepin-5(6H)-one;

3-Amino-7,9-dimethyl-6-ethylpyrido[2,3-b][1,5]benzoxazepin-5(6H)-one;

3-Amino-7,9-dimethyl-6-(n-propyl)pyrido[2,3-b][1,5]benzothiazepin-5(6H)-one;

3-Amino-7,9-dimethyl-6-(i-propyl)pyrido[2,3-b][1,5]benzothiazepin-5(6H)-one;

3-Amino-7,9-dimethyl-6-allylpyrido[2,3-b][1,5]benzothiazepin-5(6H)-one;

and pharmaceutically acceptable acid addition salts thereof.

6. A method for treating HIV-1 infection which comprises administering, to a human being who has been infected by HIV-1, a therapeutically effective amount of a compound of formula I, as set forth in claims 1, 2, 3, 4 or 5.

7. A pharmaceutical composition, suitable for the treatment of HIV-1 infection, comprising a therapeutically effective amount of a compound of formula I, as set forth in claims 1, 2, 3, 4 or 5, and a pharmaceutically acceptable carrier.

* * * * *